US012685816B2

(12) United States Patent
Yang

(10) Patent No.: US 12,685,816 B2
(45) Date of Patent: Jul. 21, 2026

(54) BILATERAL-DRIVEN PATCH-TYPE DRUG INFUSION DEVICE

(71) Applicant: MEDTRUM TECHNOLOGIES INC., Shanghai (CN)

(72) Inventor: Cuijun Yang, Shanghai (CN)

(73) Assignee: MEDTRUM TECHNOLOGIES INC., Shanghai (CN)

( * ) Notice: Subject to any disclaimer, the term of this patent is extended or adjusted under 35 U.S.C. 154(b) by 434 days.

(21) Appl. No.: 17/924,118

(22) PCT Filed: Sep. 8, 2020

(86) PCT No.: PCT/CN2020/113976
§ 371 (c)(1),
(2) Date: Nov. 9, 2022

(87) PCT Pub. No.: WO2021/227312
PCT Pub. Date: Nov. 18, 2021

(65) Prior Publication Data
US 2023/0173169 A1      Jun. 8, 2023

(30) Foreign Application Priority Data
May 14, 2020    (WO) ................ PCT/CN2020/090152

(51) Int. Cl.
A61M 5/145          (2006.01)
A61M 5/14           (2006.01)
          (Continued)

(52) U.S. Cl.
CPC ............ A61M 5/1452 (2013.01); A61M 5/14 (2013.01); A61M 5/14236 (2013.01);
          (Continued)

(58) Field of Classification Search
CPC .. A61M 2205/106; A61M 2005/14506; A61M 5/14248; A61M 5/14244;
          (Continued)

(56) References Cited

U.S. PATENT DOCUMENTS

2003/0199825 A1 * 10/2003 Flaherty .............. A61M 5/1452
                                                              604/155
2008/0319394 A1    12/2008 Yodfat et al.
          (Continued)

FOREIGN PATENT DOCUMENTS

CN          101208515          6/2008
CN          101939033          1/2011
          (Continued)

OTHER PUBLICATIONS

Machine translation of CN106110445 (Year: 2016).*

*Primary Examiner* — Theodore J Stigell
*Assistant Examiner* — Benjamin Koo
(74) *Attorney, Agent, or Firm* — JCIP GLOBAL INC.

(57)          ABSTRACT

A bilateral-driven patch-type drug infusion device comprises: an infusion unit; a driving wheel drives the screw to move by rotation, pushing the piston forward; a driving unit—includes at least two driving portions, the driving unit pivots around a pivot shaft, driving different driving portions in different direction; and an infusion tube structure, which includes a base and an infusion needle, and the base includes an initial position (L), a working position (N), and an intermediate position (M). The driving unit can drive the driving wheel in two directions for infusion drug, making the infusion unit have multiple infusion modes, enhancing user experience.

10 Claims, 5 Drawing Sheets

(51) Int. Cl.

| | |
|---|---|
| *A61M 5/142* | (2006.01) |
| *A61M 5/168* | (2006.01) |
| *A61M 5/172* | (2006.01) |
| *G16H 20/17* | (2018.01) |

(52) U.S. Cl.
CPC .... *A61M 5/14248* (2013.01); *A61M 5/16804* (2013.01); *A61M 5/172* (2013.01); *G16H 20/17* (2018.01); *A61M 2005/14208* (2013.01); *A61M 2005/14506* (2013.01); *A61M 2205/3327* (2013.01); *A61M 2205/36* (2013.01); *A61M 2230/201* (2013.01)

(58) Field of Classification Search
CPC .......... A61M 2005/14268; A61M 2005/1426; A61M 2005/14256; A61M 2005/14252; A61M 5/1452; A61M 2205/10; A61M 2205/0266
See application file for complete search history.

(56) References Cited

U.S. PATENT DOCUMENTS

| | | | | |
|---|---|---|---|---|
| 2011/0306929 | A1* | 12/2011 | Levesque .......... | A61M 5/14248 604/150 |
| 2013/0060233 | A1* | 3/2013 | O'Connor ......... | A61M 5/14248 604/151 |
| 2017/0095610 | A1 | 4/2017 | Holmes et al. | |
| 2019/0117881 | A1 | 4/2019 | Yang | |
| 2020/0147312 | A1* | 5/2020 | Gregory .............. | A61M 5/3158 |

FOREIGN PATENT DOCUMENTS

| | | | | |
|---|---|---|---|---|
| CN | 106110445 A | * 11/2016 | .............. | A61M 5/19 |
| CN | 106999670 | 8/2017 | | |
| CN | 109451730 | 3/2019 | | |

* cited by examiner

BILATERAL-DRIVEN PATCH-TYPE DRUG INFUSION DEVICE

CROSS-REFERENCE TO RELATED APPLICATION

This application is a 371 of international application of PCT application serial no. PCT/CN2020/113976, filed on Sep. 8, 2020, which claims the priority benefit of PCT application serial no. PCT/CN2020/090152, filed on May 14, 2020. The entirety of each of the above-mentioned patent applications is hereby incorporated by reference herein and made a part of this specification.

TECHNICAL FIELD

The present invention mainly relates to the field of medical instruments, in particular to a bilateral-driven patch-type drug infusion device.

BACKGROUND

A drug infusion device can continuously deliver drug into a patient's body for disease treatment. Drug infusion devices are widely used in the field of diabetes treatment, which continuously infuse required dosage of insulin into the patient's subcutaneous tissue, thereby simulating the secretion function of the pancreas to keep the blood glucose stable. The drug fluid is usually stored inside the infusion pump. The drug infusion device in prior art, controlled by remote device, is usually attached directly on the patient's skin through a medical adhesive tape.

At present, the driving method of drug infusion devices in prior art is relatively simple, which worsens user experience, making the infusion efficiency low. And air maybe infused in subcutaneous, which affects the health of users and poses safety risks.

Therefore, in the prior art, there is an urgent need for a bilateral-driven patch-type drug infusion device which can not only improve the infusion efficiency, but also prevent air from being infused into subcutaneous.

BRIEF SUMMARY OF THE INVENTION

Embodiments of the present invention provide a bilateral-driven patch-type drug infusion device with diverse driving method for infusion and higher infusion efficiency, enhancing user experience. At the same time, when the infusion tube structure is at intermediate position, the drug can exhaust the air from the infusion needle, preventing air from being infused into subcutaneous, which eliminates safety hazards and improves user experience.

The invention discloses a bilateral-driven patch-type drug infusion device, comprising: an infusion unit, which includes a drug storage unit providing with an opening for drug flowing; a screw connected to a piston and a driving wheel provided with wheel teeth, respectively, the driving wheel drives the screw to move by rotation, pushing the piston, provided in the drug storage unit, forward; a driving unit cooperating with the driving wheel, the driving unit includes at least two driving portions, the driving unit pivots around a pivot shaft, driving different driving portions in different directions, thus pushing the wheel teeth located on different driving wheel respectively, and rotating the driving wheel; a power unit, connected to the driving unit, outputs two forces in two directions on the driving unit, making the driving unit pivot in two directions around the pivot shaft; a housing, where the infusion unit is provided, includes a cavity providing with a first outlet and a second outlet, the opening is in sealed communication with the first outlet while the second outlet is sealed by an elastic seal; an infusion tube structure, which includes a base and an infusion needle fixedly arranged on the base, and the base includes an initial position, a working position, and an intermediate position set between the initial position and the working position; and a first fastener, which is used to fasten the base in order to limit the position of the base.

According to one aspect of this invention, the driving wheel includes at least two sub-wheels.

According to one aspect of this invention, the driving wheel includes two sub-wheels, and the pivot shaft is disposed between the two sub-wheels, one or more of the driving portions are provided on both sides of the driving unit, and each sub-wheel is cooperated with each driving portion.

According to one aspect of this invention, two driving portions are respectively provided on both sides of the driving unit, and the two driving portions on one side of the driving unit are disposed up and down or left and right.

According to one aspect of the present invention, the power unit includes an electric-heated linear actuator or an electric-driven linear actuator.

According to one aspect of the present invention, the driving unit has a variety of different pivot amplitudes or pivot rates, making the infusion unit have a variety of different infusion increments or infusion rates.

According to one aspect of the present invention, the type of the first fastener includes one or more of hooks, holes, blocks, or slots.

According to one aspect of the present invention, it further includes an elastic member arranged on the base or the housing, and when the base is in the working position, the elastic member is compressed.

According to one aspect of the present invention, it further includes an auxiliary resilient component, which is used to release the base, therefore under the action of the resilient force of the elastic member, the base returns to the intermediate position or the initial position from the working position.

According to one aspect of the present invention, the base includes a guide post, and the position where the base is fastened is located on the guide post.

According to one aspect of the present invention, the elastic member is a spring arranged on the housing, and a part of the guide post is located in the hollow cavity of the spring.

According to one aspect of the present invention, the first fastener is provided on the housing.

According to one aspect of the present invention, it further includes a fastening component, and the first fastener is disposed on the fastening component.

According to one aspect of the present invention, a sliding block is provided on the fastening component while the housing is provided with a groove, the sliding block is arranged in the groove, and the sliding block can slide along the groove to make the fastening component fasten or release the base.

According to one aspect of the present invention, at least one fastening arm is provided on the fastening component, and the first fastener is provided on the fastening arm.

According to one aspect of the present invention, a second fastener is provided on the housing, the first fastener is used to fasten the base at the initial position or the intermediate position while the second fastener is used to fasten the base at the work position.

According to one aspect of the present invention, the infusion needle includes a front end and a subcutaneous end, both the front end and the subcutaneous end extend out of the base, wherein: when the base is at the initial position, the front end is not communicated with the second outlet; when the base reaches the intermediate position or the working position, the front end pierces the elastic seal to communicate with the second outlet, and the drug, along the cavity, flows from the drug storage unit to the subcutaneous end.

Compared with the prior arts, the technical solution of the present invention has the following advantages:

In the bilateral-driven patch-type drug infusion device disclosed herein, a power unit connected to the driving unit, the power unit outputs two forces in two directions on the driving unit, making the driving unit pivot in two directions around the pivot shaft. The driving unit can drive the driving wheel in two directions for infusion drug, improving the infusion efficiency. Additionally, with the driving unit pivoting in two directions, the infusion unit has multiple infusion modes. At the same time, the infusion tube structure includes a base and an infusion needle fixedly arranged on the base, and the base includes an initial position, a working position, and an intermediate position set between the initial position and the working position. Setting an intermediate position between the initial position and the working position makes the infusion needle filled with drug before it enters subcutaneous, preventing air from entering the subcutaneous, therefore, eliminating potential safety hazards.

Furthermore, the driving unit has a variety of different pivot amplitudes or pivot rates, making the infusion unit have a variety of different infusion increments or infusion rates. Controlled by the program unit, the driving unit can pivot with different amplitudes; also, the driving unit has multiple pivot rates, changing the infusion rates of the infusion unit. And according to body condition, user can chose suitable or different infusion modes, optimizing the infusion process and accurately controlling the blood glucose level.

Furthermore, the infusion device also includes an elastic member, which is arranged on the base or on the housing, and when the base is in the working position, the elastic member is compressed. Before the infusion device is torn off, the subcutaneous end of the infusion needle can be retracted into the housing by the elastic member to avoid scratching the skin and improve user experience.

BRIEF DESCRIPTION OF THE DRAWINGS

FIG. 2b is a side view of the driving unit in FIG. 2a;

4

Figure 5A:
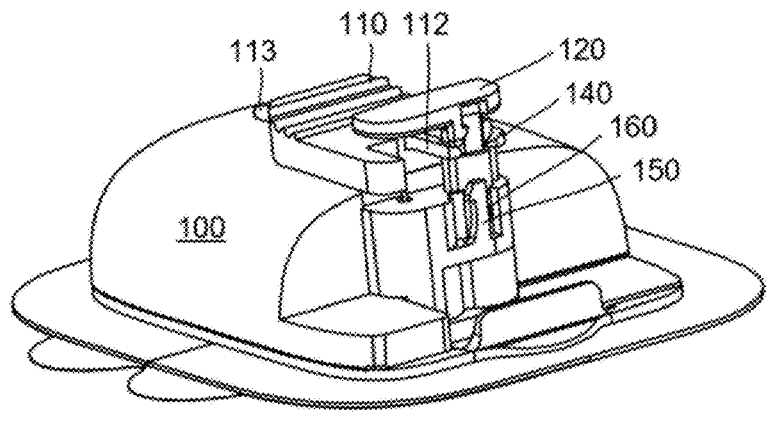
FIG. 5a is a schematic view of a part of the structure of the infusion device according to an embodiment of the present invention.
Figure 5B:
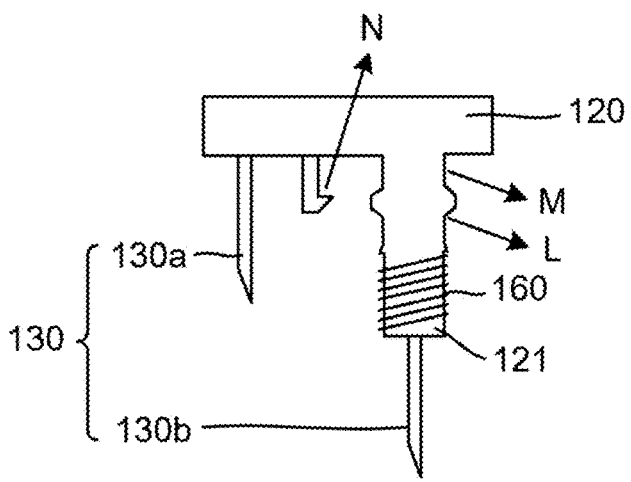
Figure 5C:
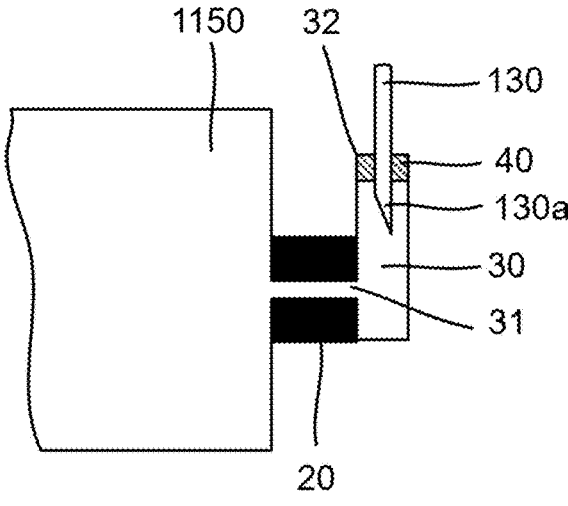
Figure 6:
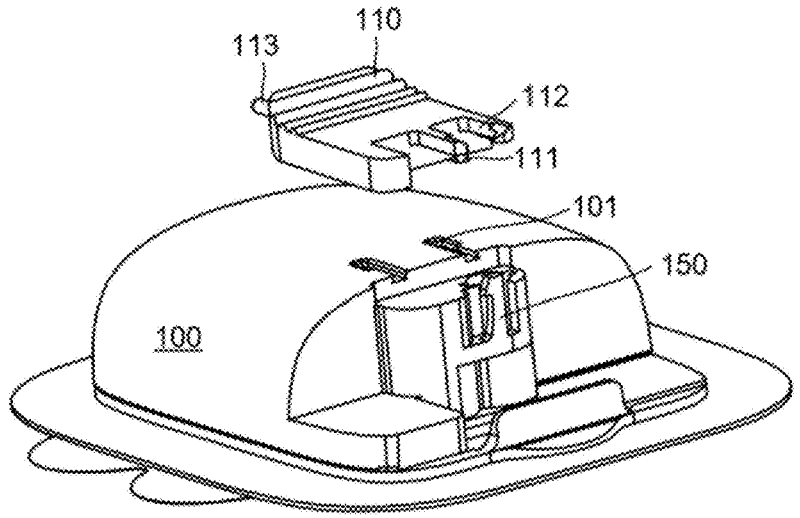
Figure 7:
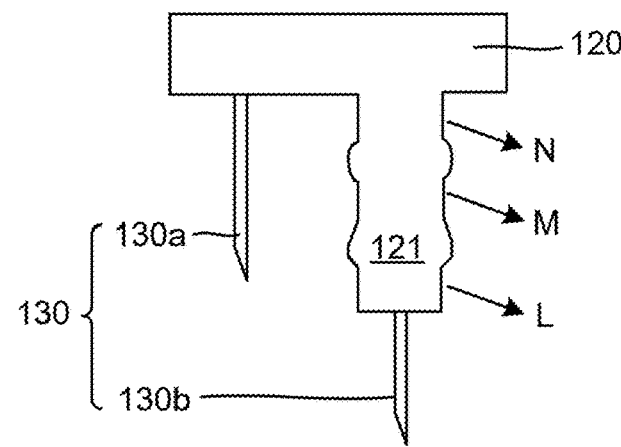
Figure 8:
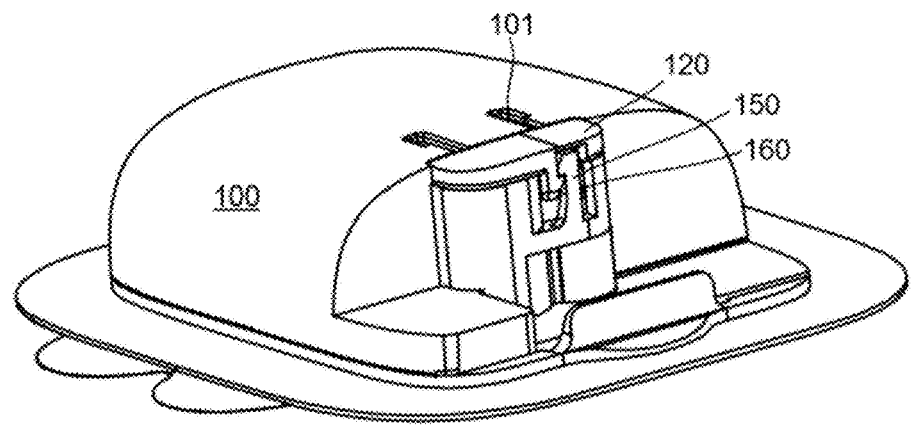

FIG. 5b is a schematic view of an infusion tube structure according to an embodiment of the present invention;

FIG. 5c is a schematic view of the drug storage unit and the cavity according to the embodiment of this present invention;

FIG. 6 is a schematic view of the fastening component separated from the housing according to an embodiment of the present invention;

FIG. 7 is a schematic view of an infusion tube structure according to another embodiment of the present invention;

FIG. 8 is a schematic view of the base in the working position according to an embodiment of the present invention.

DETAILED DESCRIPTION

As mentioned above, the driving method of drug infusion devices in prior art is relatively simple, which worsens user experience, making the infusion efficiency low. And air maybe infused in subcutaneous, which affects the health of users and poses safety risks.

Studies have found that the reasons for the above problems are that the driving unit can only drive the driving wheel in one rotation direction, and air exists in the cavity of the infusion needle when it penetrates into subcutaneous.

In order to solve this problem, the present invention provides a bilateral-driven patch-type drug infusion device. The driving unit can drive the driving wheel in two directions for infusion drug, making the infusion unit have multiple infusion modes, enhancing user experience. At the same time, when the infusion tube structure is at intermediate position, the drug can exhaust the air in the infusion needle, preventing air from being infused into subcutaneous, which eliminates safety hazards and improves user experience.

Various exemplary embodiments of the present invention will now be described in detail with reference to the drawings. The relative arrangement of the components and the steps, numerical expressions and numerical values set forth in the embodiments are not to be construed as limiting the scope of the invention.

In addition, it should be understood that, for ease of description, the dimensions of the various components shown in the figures are not necessarily drawn in the actual scale relationship, for example, the thickness, width, length or distance of certain units may be exaggerated relative to other structures.

The following description of the exemplary embodiments is merely illustrative, and is not intended to be in any way limiting the invention and its application or use. The techniques, methods and devices that are known to those of ordinary skill in the art may not be discussed in detail, but such techniques, methods and devices should be considered as part of the specification.

It should be noted that similar reference numerals and letters indicate similar items in the following figures. Therefore, once an item is defined or illustrated in a drawing, it will not be discussed further in the following description of the drawings.

Figure 1A:
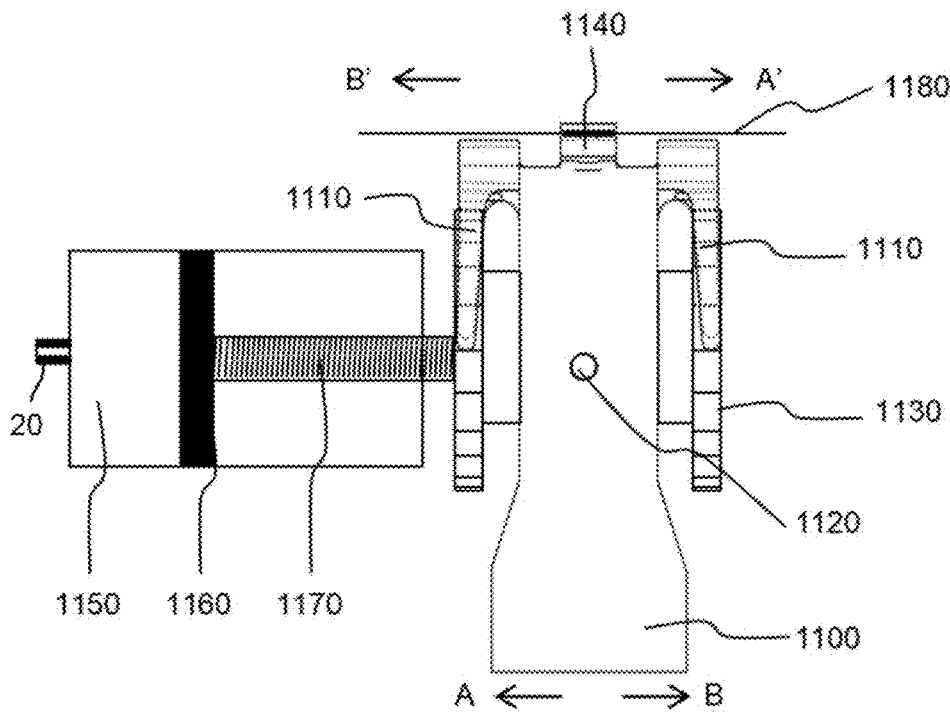
FIG. 1a-FIG. 1b are schematic views showing the structure of the infusion unit according to an embodiment of the present invention.
Figure 1B:
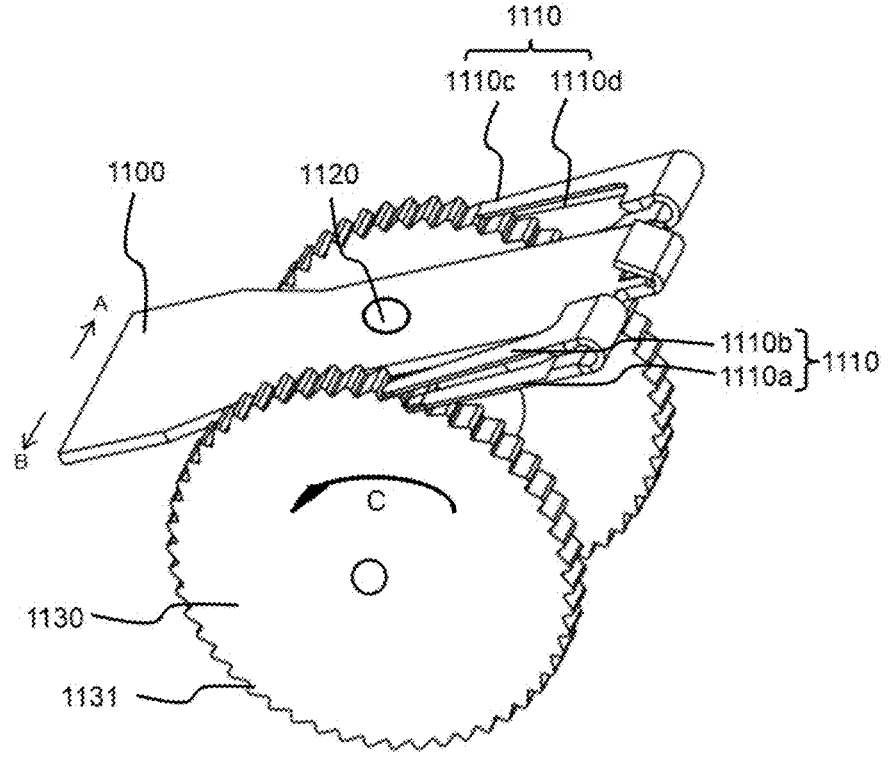

FIG. 1a is a schematic view showing the structure of the infusion unit according to an embodiment of the present invention. FIG. 1b is a schematic view of the cooperation between the driving unit 1100 and the driving wheel 1130 according to an embodiment of the present invention.

The infusion unit includes a driving unit 1100, a driving wheel 1130, a drug storage unit 1150, a piston 1160, a screw 1170, and a power unit 1180.

The drug storage unit 1150 is used for storing liquid drug. Drugs include, but are not limited to, insulin, glucagon, antibiotics, nutrient solutions, analgesics, morphine, anticoagulants, gene therapy drugs, cardiovascular drugs or chemotherapy drugs, etc. Preferably, in the embodiment of this present invention, the drug is insulin.

The piston 1160 is used to infuse drugs into the body.

The screw 1170 is connected to the piston 1160 and the driving wheel 1130, respectively. In the embodiment of the present invention, the driving wheel 1130 is movably mounted on the device base (not shown), and the driving wheel 1130 moves the driving screw 1170 through rotation to advance the piston 1160 disposed in the drug storage unit 1150 to move forward for the purpose of injecting drug.

The driving unit 1100 is used to drive the driving wheel 1130 to rotate. The driving unit 1100 is movably connected to the device base through the pivot shaft 1120. The power unit 1180 is used to apply a force to the driving unit 1100 leading the driving unit 1100 to pivot. In the embodiment of the present invention, the power unit 1180 is fixedly connected at the top position 1140 of the driving unit 1100, thereby dividing the power unit 1180 into two left and right portions, such as the A' direction portion and the B' direction portion in FIG. 1*a*. The driving unit 1100 is alternately led to pivot in the A' direction or the B' direction through the pivot shaft 1120. Preferably, in the embodiment of the present invention, when the power unit 1180 leads the driving unit 1100 to A' direction, the driving unit 1100 pivots in the A direction through the pivot shaft 1120, while the power unit 1180 leads the driving unit 1100 to the B' direction, the driving unit 1100 pivots in the B direction through the pivot shaft 1120. By alternately leading the driving unit 1100 to the A' direction and the B' direction, the driving unit 1100 can be alternately pivoted through the pivot shaft 1120 in two different directions, like the A direction and the B direction.

The power unit 1180 includes an electric-heated linear actuator or an electric-driven linear actuator. Preferably, in the embodiment of the present invention, the power unit 1180 is made of shape memory alloy. The A' direction portion and the B' direction portion of the shape memory alloy are alternately powered on and off, and a force is applied to the driving unit 1100 by a change in the length of the power unit 1180 thereof. The power unit 1180 may be composed of one piece of shape memory alloy, or may be composed of left and right segments (such as the A' direction segment and the B' direction segment) of shape memory alloy, which is not specifically limited herein, as long as the force can be applied to lead the driving unit 1100 to pivot.

Here, it should be noted that the power unit 1180 includes, but is not limited to, a shape memory alloy. In other embodiments of the present invention, the power unit 1180 may also be other structures, and the location where the power unit 1180 applies force to the driving unit 1100 is neither limited to the top position 1140, as long as the action of applying a force to the driving unit 1100 can be satisfied to cause the driving unit 1100 to alternately pivot left and right.

As shown in FIG. 1*a* and FIG. 1*b*, the driving wheel 1130 includes a plurality of sub-wheels, and the circumferential surface of the sub-wheels is provided with wheel teeth 1131. Driving unit 1100, through the wheel teeth 1131, cooperates with the driving wheel 1130.

In the embodiment of the present invention, a plurality of driving portions 1110 are installed on each side of the driving unit 1100. Therefore, a plurality of sub-wheels are also installed on both sides of the driving unit 1100 to cooperate with the driving portions 1110. Preferably, in the embodiment of the present invention, the driving unit 1100 includes four driving portions 1110, which are 1110*a*, 1110*b*, 1110*c*, and 1110*d*, respectively. 1110*a*, 1110*b* are installed on one side of the driving unit 1100 while 1110*c*, 1110*d* are on the other side. The driving wheel 1130 includes two sub-wheels, one of which cooperates with 1110*a*, 1110*b* and the other of which cooperates with 1110*c*, 1110*d*.

Figure 2A:
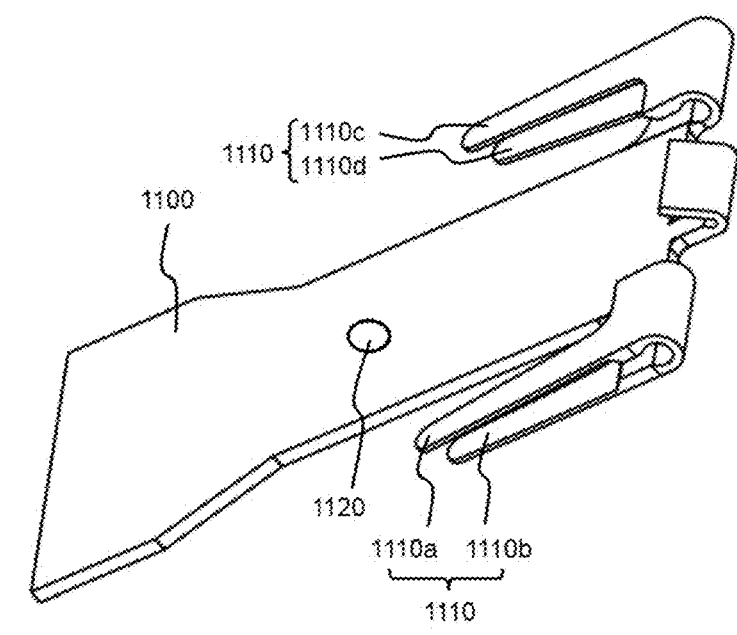
FIG. 2a is a schematic view of the driving unit according to an embodiment of the present invention.
Figure 2B:
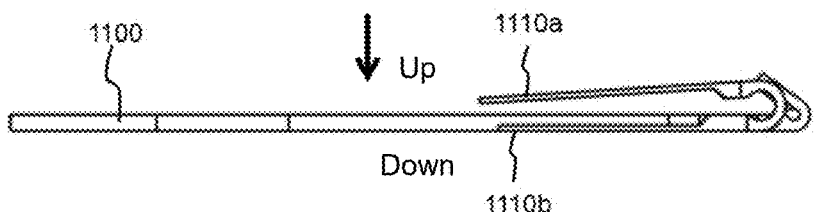

FIG. 2*a* and FIG. 2*b* are respectively schematic view, a side view of the driving unit 1100.

In the embodiment of the present invention, the two driving portions 1110 on one side of the driving unit 1100 are installed up and down. Here, the up and down setting refers to the up and down positional relationship representations shown in FIG. 2*b*. Preferably, the two driving portions 1110 (such as 1110*a* and 1110*b*) on the side of the driving unit 1100 can be seen in the side view FIG. 2*b*, and 1110*b* and 1110*d* are blocked by 1110*a* and 1110*c*, respectively.

It should be noted that, in other embodiments of the present invention, these four driving portions may be disposed by other means, such as the two driving portions on one side of the driving unit are disposed left and right, as long as the arms are able to drive the driving wheel to rotate, which is not specifically limited herein.

Figure 3:
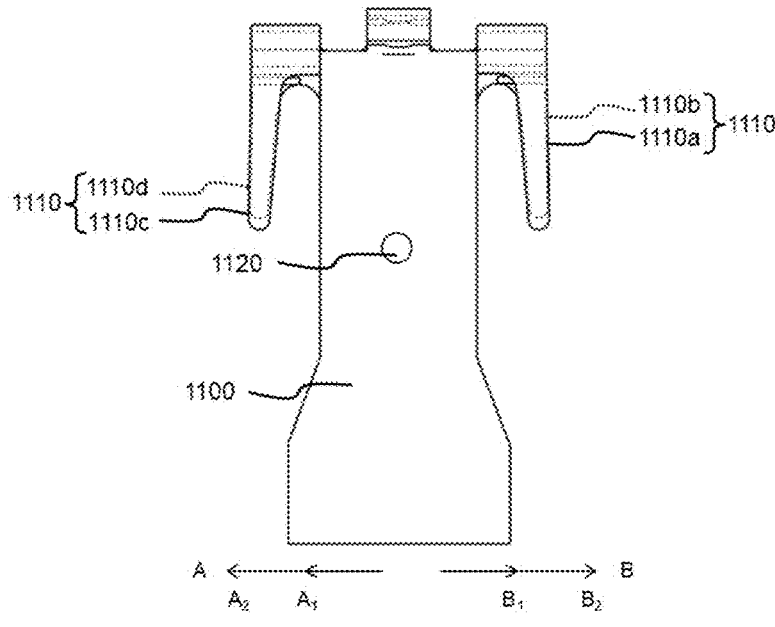
FIG. 3 is a schematic view of a position structure of multiple pivot amplitudes of the driving unit according to an embodiment of the present invention.

FIG. 3 is a schematic view of a position structure of a plurality of pivot amplitudes of the driving unit 1100, and is also a top view in the direction of the arrow in FIG. 2*b*.

In a single pivot in the direction A, driving portion 1110*a* and/or 1110*b* engage the wheel teeth 1131 to rotate the driving wheel 1130 while 1110*c* and 1110*d* can slide on the wheel teeth 1131, but not exert a force for driving the driving wheel 1130 to rotate. And obviously, 1110*c* slides to the next adjacent driving position firstly. At this time, the driving unit 1100 stops pivoting and the driving portions 1110*a* and/or 1110*b* stop engaging the wheel teeth 1131, therefore, the driving wheel 1130 stops rotating. Thus, the driving unit 1100 completes one kind of pivot amplitude. At this time, the driving unit 1100 pivots to reach $A_1$ position in the A direction. The next moment the driving unit 1100 continues to pivot in the A direction, 1110*d* will slide to the next adjacent driving position. Similarly, the driving unit 1100 completes another kind of pivot amplitude. At this time, the driving unit 1100 still pivots in the A direction to reach $A_2$ position. And the driving unit 1100 completes the whole process of single pivot in the A direction, performing $A_1$ and $A_2$ two pivot amplitudes, respectively, thereby driving the driving wheel 1130 to rotate by two steps, realizing two kinds of infusion modes of the infusion unit.

It should be noted that, in the above pivoting process, the driving portion 1110*d* may firstly slide to the next wheel tooth 1131, and then 1110*c* slides to the next wheel tooth 1131, which is not specifically limited herein. Similarly, when the driving unit 1100 pivots in the B direction, it can perform $B_1$ and $B_2$ two pivot amplitudes, respectively.

Obviously, in the whole process of the above-mentioned single pivot in the A direction, the driving unit 1100 undergoes an alternate action of pivot and stop, and the driving portions 1110 alternately engage and stop engaging wheel teeth 1131 to drive the driving wheel 1130 to rotate and stop rotating, realizing two-step rotation of the driving wheel, and finally achieving two infusion modes of the infusion unit.

Referring to FIG. 3 again, in another embodiment of the present invention, the driving unit 1100 pivots to the $A_1$ position, and then pivots one or two amplitudes in the B direction, that is, reaching the $B_1$ or $B_2$ position until the pivot in the B direction stops. This process completes the alternate pivot of the driving unit 1100 in two directions, so that the driving wheel 1130 can be rotated in multiple steps. Therefore, in the embodiment of the present invention, the driving unit 1100 can alternately switch amplitudes among $A_1$-$B_1$, or $A_1$-$B_1$-$B_2$, or $B_1$-$A_1$-$A_2$, so as to achieve the purpose of switching among different infusion modes.

Referring to FIG. 3 again, in another embodiment of the present invention, the driving unit 1100 can also be pivoted directly to the $A_2$ position without stopping at $A_1$ position, then directly pivoted to the $B_2$ position without stopping at $B_1$ position, that is, the driving unit 1100 alternately pivots between the $A_2$-$B_2$ positions. As described above, the driving unit 1100 can also alternately pivot between the $A_1$-$B_1$ positions.

As with the infusion unit of the embodiment of the present invention, when the infusion is started, the amount of drug required is relatively large, so the patient or the artificial pancreas can select the large $A_2$-$B_2$ pivot amplitude for infusion. After a period of time, the intermediate $A_1$-$B_1$-$B_2$ pivot amplitude or $B_1$-$A_1$-$A_2$ pivot amplitude can be used to reduce the rate of drug infusion. When the drug infusion is about to be completed, the patient or the artificial pancreas can switch to the small $A_1$-$B_1$ pivot amplitude to further reduce the infusion rate and achieve precise control of the drug infusion. Of course, the patient or the artificial pancreas can also choose one mode or several modes for infusion, and there are no specific restrictions.

It should be noted that in another embodiment of the present invention, further more driving portions, like three, four, etc., can be disposed on one side of the driving unit. And the total number of driving portions may also be an odd number, such as three, five or more, that is, the numbers of driving portions on both sides of the driving unit are not equal. Moreover, the structural relationship between the different driving portions can be similar to that described above, and no specific restrictions are imposed herein.

Figure 4A:
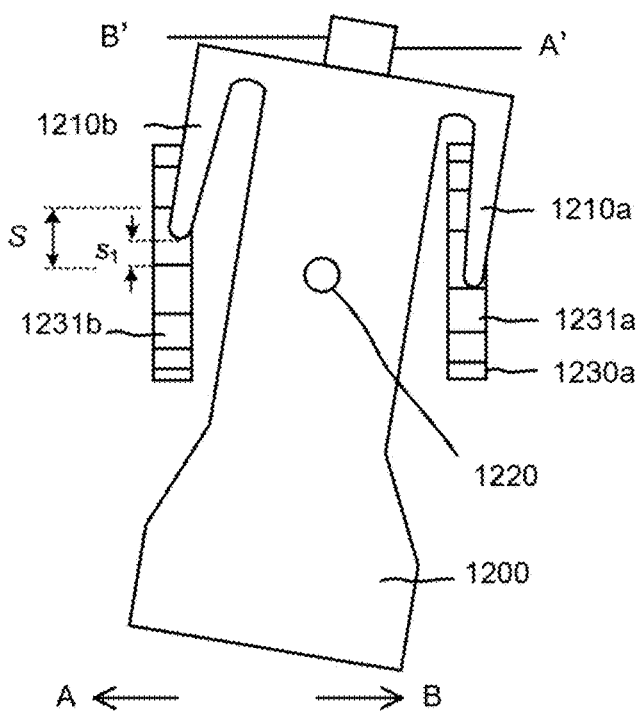
FIG. 4a-FIG. 4b are schematic views of the driving unit including two driving portions according to another embodiment of the present invention.
Figure 4B:
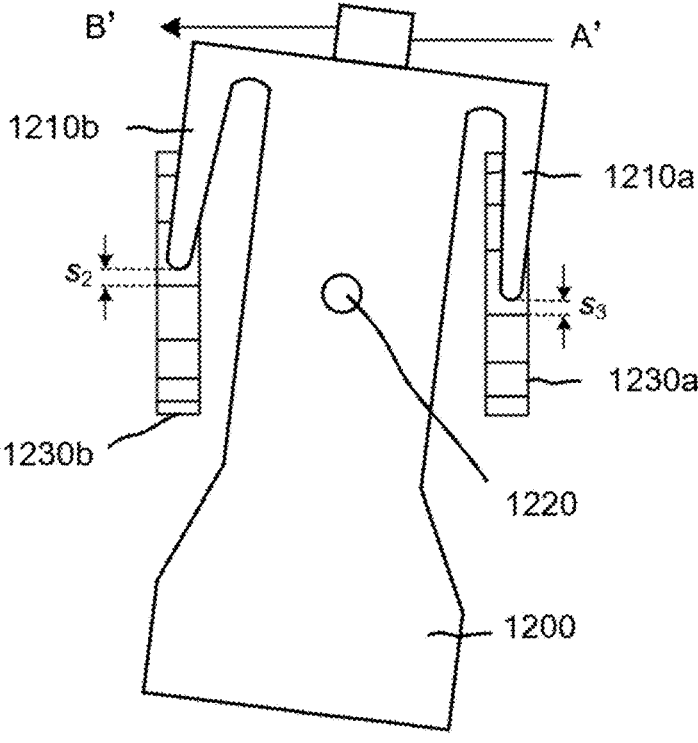

FIG. 4*a*-FIG. 4*b* are schematic views of the driving unit 1200 including two driving portions.

As described above, when the driving unit 1200 is output a force in the A' direction, the driving unit 1200 rotates in the A direction around the pivot shaft 1220, making the driving portion 1210*a* push the wheel teeth 1231*a*, thereby driving the driving wheel 1230*a* to rotate. When the driving unit 1200 is output a force in the B' direction, the driving unit 1200 rotates in the B direction around the pivot shaft 1220, making the driving portion 1210*b* push the wheel teeth 1231*b*, thereby driving the driving wheel 1230*b* to rotate.

Referring to FIG. 4*a* and FIG. 4*b* again, when the driving portion 1210*a* or 1210*b* reaches a different position, the driving unit 1200 can still continue to rotate in the direction A or B to move the driving portion away from the driving position. If the distance of the driving portion 1210*a* away from the driving position is $s_1$, if the tooth pitch is S, then $s_1$=1/3S, 1/2S, 3/4S, or S. Therefore, during the pivot of the driving unit 1200, at a certain moment, neither of the driving portions 1210*a* and 1210*b* push the wheel teeth 1231, for example, the front end of the driving portion and the driving position are separated by $s_2$ and $s_3$, respectively. At this time, the driving wheel does not rotate, nor does the infusion unit perform drug infusion. According to this working principle, the driving unit 1200 will pivot at any different amplitude, and the infusion unit has a variety of different infusion modes.

In the embodiments of the present invention, the frequency of the force output by the power unit can be changed to further change the pivot frequency of the driving unit, so that the infusion unit has a variety of different infusion rates.

The user or the artificial pancreas can flexibly select the appropriate infusion rate as needed, making the infusion process flexible and controllable.

FIG. 5*a* is a schematic view of a part of the structure of the infusion device according to an embodiment of this present invention. FIG. 5*b* is a schematic view of an infusion tube structure according to an embodiment of this present invention. FIG. 5*c* is a schematic view of the drug storage unit 1150 and the cavity 30 according to the embodiment of the present invention.

As shown in FIG. 5*a*, the infusion device of the embodiment of the present invention includes a housing 100 where the infusion unit is provided. The infusion tube structure, arranged on the housing 100, is used to fixedly place the infusion needle 130, making the drug flow into subcutaneous.

As shown in FIG. 5*b*, the infusion tube structure includes an infusion needle 130 and a base 120. The infusion needle 130 is fixedly placed on the base 120. The infusion needle 130 includes a front end 130*a* and a subcutaneous end 130*b*, both of which extend out of the base 120. The front end 130*a* is used to communicate with the opening 20 of the drug storage unit 1150, while the subcutaneous end 130*b* is used to penetrate into the subcutaneous.

As shown in FIG. 5*c*, the housing 100 is further provided with a cavity 30 including a first outlet 31 and a second outlet 32. The first outlet 31 is in sealed communication with the opening 20. Here, the sealed communication means that the cavity 30 and the drug storage unit 1150 are in communication with each other through the opening 20 and the first outlet 31 without drug leaking. The second outlet 32 is sealed by an elastic seal 40. When the front end 130*a* pierces the elastic seal 40, the infusion needle 130, the cavity 30, the opening 20 and the drug storage unit 1150 are in communication. Therefore, the drug can enter the infusion needle 130 from the drug storage unit 1150 to the subcutaneous end 130*b* or be infused subcutaneously, as shown in FIG. 5*c*.

Please continue to refer to FIG. 5*a* and FIG. 5*b*, in the embodiment of the present invention, the base 120 has three positions: an initial position, an intermediate position, and a working position. Among them, the intermediate position is set between the initial position and the working position. Since the infusion needle 130 is fixed on the base 120, in the embodiment of the present invention, the infusion tube structure also has the above three positions.

Preferably, in the embodiment of the present invention, when the base 120 is at initial position, the front end 130*a* does not pierce the elastic seal 40, so it is not communicated with the second outlet 32. When the base 120 reaches the intermediate position or the working position, the front end 130*a* pierces the elastic seal 40 communicating with the second outlet 32. At this time, the drug, along the cavity 30 and the infusion needle 130, flows from the drug storage unit 1150 to the subcutaneous end 130*b*.

At the beginning, the base 120 is at the initial position with the infusion needle 130 non-communication with the drug storage unit 1150. Therefore, the cavity of the infusion needle 130 is full filled with air. When leaving the factory, the non-communication between the infusion needle 130 and the drug storage unit 1150 can improve the flexibility of the setting position of the infusion needle 130, which optimizes the structural design of the infusion device.

After the base 120 reaches the intermediate position, the front end 130*a* pierces the elastic seal 40 in order to make the infusion needle 130 communicate with the drug storage unit 1150. At this time, when the infusion unit is activated, the drug can flow, along the infusion needle 130, to the subcutaneous end 130*b*, exhausting the air in the cavity of the infusion needle 130. Then, when the base 120 reaches the working position, the subcutaneous end 130*b* enter into subcutaneous to inject the drug into the body. Since the air in the infusion needle 130 has been exhausted earlier, no air will be infused into subcutaneous when the base 120 reaches the working position, thereby eliminating potential safety hazards.

In order to ensure that the infusion tube structure can reach different positions, the infusion device of the present invention is also provided with a first fastener 140 which is used to fasten the base 120 at the above-mentioned different positions. The type of the first fastener 140 includes one or more of hooks, holes, blocks, and slots. Preferably, in the embodiment of the present invention, the first fastener 140 is a hook.

Please continue to refer to FIG. 5*b*, in the embodiment of the present invention, the base 120 also includes a guide post 121. The position where the base 120 is fastened by the first fastener 140 is located on the guide post 121. For example, when the base 120 is fastened at position L, the base 120 is at the initial position; and when fastened at position M, the base 120 is at the intermediate position.

Please continue to refer to FIG. 5*a*, in the embodiment of the present invention, the infusion device further includes a fastening component 110 which is used to limit the position of the base 120. Therefore, the first fastener 140 is disposed on the fastening component 110. Preferably, in the embodiment of the present invention, a fastening arm 112 is provided on the fastening component 110. And the first fastener 140 is disposed on the fastening arm 112.

When the base 120 is at the initial position, the first fastener 140 is fastening at position L. Directly pressing the top of the base 120 with a finger makes the first fastener 140 fasten the guide post 121 at position M, so that the base 120 reaches the intermediate position.

It should be noted that the base 120 may not be provided with the guide post 121, but a structure capable of fastening with each other is provided on the side wall of the base 120, which is not specifically limited here, as long as the base 120 can reach different position.

Preferably, in the embodiment of the present invention, the use of the fastening component 110 can only fasten the base 120 at the initial position and the intermediate position. In addition, the base 120 cannot reach the working position due to the fastening component 110. At the same time, a second fastener 150 is provided on the housing 100 which is used to fasten the base 120 at position N, in order to make the base 120 fastened at the working position.

FIG. 6 is a schematic view of the fastening component 110 separated from the housing 100 according to an embodiment of the present invention.

The fastening component 110 of the embodiment of the present invention includes a slider 111. The housing 100 is provided with a groove 101 where the slider 111 is arranged. The fastening component 110 can slide along the groove 101 to fasten the base 120 or release it. Preferably, in the embodiment of the present invention, after the sliding fastening component 110 releases the base 120, the fastening component 110 can be removed from the housing 100, as shown in FIG. 8.

Therefore, the working principle of the base 120 reaching these three positions in the embodiment of the present invention is as follows. At the beginning, the infusion device is not attached to the skin surface. And the first fastener 140 is fastening the guide post 121 at position L, so the base 120 is at the initial position. At this time, the front end 130*a* does not pierce the elastic seal 40, so that the infusion needle 130 is not in communication with the drug storage unit 1150. Then, directly pressing the top of the base 120 with a finger makes the first fastener 140 fasten the guide post 121 at position M, so the base 120 is in the intermediate position. Although the infusion device is still not attached to the skin surface, the front end 130*a* of the infusion needle pierces the elastic seal 40 making the infusion needle 130 communicate with the drug storage unit 1150. Therefore, the drug can flow in the cavity of the infusion needle 130 and exhaust air in the infusion needle 130. At this position, the subcutaneous end 130*b* does not extend or slightly extends out of the housing 100. Then attach the infusion device on the skin surface. And slide the fastening component 110 backward to release the base 120. Continue to press the top of the base 120 so that the second fastener 150 fastens the guide post 121 at position N. Therefore, the base 120 is in the working position, and the subcutaneous end 130*b* penetrates the subcutaneous. Obviously, the infusion needle 130 is communicated with the drug storage unit 1150, and the drug can be injected into subcutaneous.

FIG. 7 is a schematic view of an infusion tube structure according to another embodiment of the present invention.

In another embodiment of the present invention, the infusion device may not be provided with the fastening component 110 and the second fastener 150, but the first fastener (not shown at this time) is directly provided on the housing 100. At this time, the initial position L, the intermediate position M and the working position N are all located on the guide post, as shown in FIG. 7. When the base 120 is at the initial position, the first fastener is fastening at position L.

When the top of the base 120 is pressed, the base 120 moves downward, the first fastener is fastening at position M, helping the base 120 reach the intermediate position. Continue to press the top of the base 120, in order to make the base 120 continue to move downwards. The first fastener is fastening at position N, making the base 120 reach in the working position. This design reduces the number of structures in the infusion device and facilitates user operation.

FIG. 8 is a schematic view of the base 120 in the working position according to the embodiment of this present invention.

The infusion device also includes an elastic member 160 provided on the base 120 or on the housing 100. Preferably, in the embodiment of the present invention, the elastic member 160 is a spring provided on the housing 100, and a part of the guide post 121 is located in the hollow cavity of the spring (as shown in FIG. 5*b*). When the base 120 is in the working position, the elastic member 160 is compressed, thereby generating a resilient force.

In other embodiments of the present invention, the elastic member 160 may also be a structure such as elastic silicone, elastic sheet, etc., which is not specifically limited here. As in an embodiment of the present invention, the elastic member 160 is disposed on the base 120, and the elastic member 160 interacts with one structure of the housing 100 to generate a resilient force.

As mentioned above, when the base 120 is in the working position, the subcutaneous end 130*b* is pierced into subcutaneous. If the subcutaneous end 130*b* does not retract into the infusion device when the infusion device is torn off from the skin surface, the end of the subcutaneous end 130*b* is likely to scratch the skin, causing additional trauma and poor user experience. Therefore, the subcutaneous end 130*b* of the infusion needle can be retracted, by the resilient force of the elastic member 160, into the housing 100 before the infusion device is torn off, which avoids scratching the skin and improves user experience.

Preferably, in the embodiment of the present invention, the infusion device further includes an auxiliary resilient component 113 (as shown in FIG. 5*a* and FIG. 6) which is used to release the base 120. After the fastened base 120 is released, the base 120 can return to the intermediate position or the initial position under the action of the resilience of the spring.

The embodiment of the present invention does not limit the type of the auxiliary resilient component 113 and the manner or position for releasing the base 120. As in the embodiment of the present invention, the auxiliary resilient component 113 is provided at one end of the fastening component 110. The auxiliary resilient component 113 can be inserted into the housing 100 to change the position of the second fastener 150 to release the base 120. In another embodiment of the present invention, the auxiliary resilient component 113 can enter the inside of the housing 100 from a hole (not shown) provided on the top of the base 120, thereby changing the position of the second fastener and releasing the base 120. In still another embodiment of the present invention, an additional sliding button connected to the second fastener may be provided. The user can slide the sliding button with a finger to release the base 120.

It should be noted that, in other embodiments of the present invention, the manner in which the base 120 reaches different positions can also be automatically controlled by a program. Therefore, the user does not need to manually operate with a finger, which is not specifically limited here.

In summary, the present invention provides a bilateral-driven patch-type drug infusion device. The power unit outputs a controllable and stable driving force to drive the driving portion forward, thereby pushing the wheel teeth forward, avoiding the drug blockage. At the same time, before the infusion device is attached on the skin surface, the drug can exhaust the air in the infusion needle, preventing air from being infused into subcutaneous, which eliminates safety hazards and improves user experience.

While the invention has been described in detail with reference to the specific embodiments of the present invention, it should be understood that it will be appreciated by those skilled in the art that the above embodiments may be modified without departing from the scope and spirit of the invention. The scope of the invention is defined by the appended claims.

The invention claimed is:

1. A bilateral-driven patch-type drug infusion device, comprising:

an infusion unit, comprising:

a drug storage unit provided with an opening for drug flowing;

a screw connected to a piston and a driving wheel provided with wheel teeth, respectively, the driving wheel drives the screw to move by rotation to push the piston in the drug storage unit to move forward;

a driving unit cooperated with the driving wheel, the driving unit comprises at least two driving portions, the driving unit pivots around a pivot shaft to drive different driving portions of the at least two driving portions in different directions, thus pushing the wheel teeth located on different driving wheel respectively, and rotating the driving wheel; and a power unit, connected to the driving unit, outputs two forces in two directions on the driving unit to make the driving unit pivot in two directions around the pivot shaft;

a housing, where the infusion unit is provided, includes a cavity providing with a first opening and a second opening, the opening of the drug storage unit is connected with the first opening, wherein the second opening is surrounded by an elastic seal;

an infusion tube structure, which comprises a base and an infusion needle fixedly arranged on the base, and the base comprises an initial position, a working position, and an intermediate position set between the initial position and the working position, wherein the base comprises a guide post, when the base is at the initial position, the base is fastened to the housing at a first position along the guide post, when the base is at the intermediate position, the base is fastened to the housing at a second position along the guide post, and when the base is at the working position, the base is fastened to the housing at a third position of the base;

an elastic member arranged on the base or the housing, and when the base is in the working position, the elastic member is compressed;

a fastening component, which comprises a first fastener and an auxiliary resilient component, wherein the first fastener is used to fasten the base to the housing at the first position or the second position; and a second fastener is provided on the housing, after sliding the fastening component backward to release the base, the second fastener fastens the base at the third position, wherein, by inserting the auxiliary resilient component into the housing, a position of the second fastener is changed, thereby releasing the base from the second fastener and returning the base to the intermediate position or the initial position from the working position, the infusion needle comprises a front end and a subcutaneous end, both the front end and the subcutaneous end extend out of the base, wherein:

when the base is at the initial position, the front end is not communicated with the second opening;

when the base reaches the intermediate position, the front end pierces the elastic seal to communicate with the second opening, and the drug, along the cavity, flows from the drug storage unit to the subcutaneous end, to exhaust air in the cavity of the infusion needle.

2. The bilateral-driven patch-type drug infusion device of claim 1, wherein the driving wheel comprises at least two sub-wheels.

3. The bilateral-driven patch-type drug infusion device of claim 2, wherein the driving wheel comprises two sub-wheels, and the pivot shaft is disposed between the two sub-wheels, one or more of the driving portions are provided on both sides of the driving unit, and each sub-wheel is cooperated with each driving portion.

4. The bilateral-driven patch-type drug infusion device of claim 3, wherein two driving portions are respectively provided on both sides of the driving unit, and the two driving portions on one side of the driving unit are disposed up and down or left and right.

5. The bilateral-driven patch-type drug infusion device of claim 1, wherein the power unit comprises an electric-heated linear actuator or an electric-driven linear actuator.

6. The bilateral-driven patch-type drug infusion device of claim 1, wherein the driving unit has a variety of different pivot amplitudes or pivot rates, and the infusion unit have a variety of different infusion increments or infusion rates.

7. The bilateral-driven patch-type drug infusion device of claim 1, wherein the type of the first fastener comprises one or more of hooks, holes, blocks, or slots.

8. The bilateral-driven patch-type drug infusion device of claim 1, wherein the elastic member is a spring arranged on the housing, and a part of the guide post is located in a hollow cavity of the spring.

9. The bilateral-driven patch-type drug infusion device of claim 1, wherein a slider is provided on the fastening component while the housing is provided with a groove, the slider is arranged in the groove, and the slider can slide along the groove to make the fastening component fasten or release the base.

10. The bilateral-driven patch-type drug infusion device of claim 1, wherein the fastening component further comprises at least one fastening arm, and the first fastener is provided on the fastening arm.

* * * * *